United States Patent [19]

Olesen et al.

[11] Patent Number: Plant 6,264

[45] Date of Patent: Aug. 30, 1988

[54] ROSE PLANT NAMED POULMAN

[76] Inventors: Pernille Olesen; Mogens N. Olesen, both of Hillerodvej 49, DK 3480 Fredensborg, Denmark

[21] Appl. No.: 907,373

[22] Filed: Sep. 15, 1986

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Vincent G. Gioia

[57] ABSTRACT

A new currant red hybrid tea rose of good form.

1 Drawing Sheet

The present invention relates to a new and distinct variety of rose plant of the hybrid tea rose class, which was originated by my crossing as seed parent the rose known as "Precious Platinum" and as pollen parent an unnamed, unpatented rose of my creation. The denomination of this new rose is "Poulman".

Among the novel characteristics possessed by this new variety which distinguish it from its parents and all other varieties of which I am aware are its attractive, high centered currant red to cardinal red flowers which retain their coloring upon aging. Flowers are of good exhibition form and are desirable for cutting as well as garden decoration, lasting many days on the plant or after cutting. Asexual reproduction by budding of the new variety as performed in Fredensborg, Denmark, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description hereinrefers to plate numbers in the aforementioned color chart, e.g., "46A" is plate 46A of the Royal Horticultural Society Colour Chart.

Parentage: Seedling.

*Seed parent.*—"Precious Platinum".

*Pollen parent.*—Unnamed seedling.

Class: Hybrid Tea.

The following observations are made of specimens grown outdoors in Fredensborg, Denmark, during the month of October.

FLOWER

Blooming habit: Recurrent.

Bud:

(1) *Size.*—Large, about 45 mm.

(2) *Form.*—Pointed.

(3) *Color.*—As sepals divide, buds are currant red, near 46A.

(4) *Sepals.*—About same length as bud (5) *Peduncle.*—Length — long. Aspect — straight. Strength — erect, strong. Color — reddish green.

B. Bloom:

(1) *Size.*—Average size when fully expanded — about 8 to 10 cm.

(2) *Borne.*—Primarily singly, but often with side buds.

(3) *Form.*—High centered, pointed bud opens with good high center, exhibition form, outer petals roll under and are often notched.

(4) Petalage.—Number of petals under normal conditions — about 30 to 35.

(5) Color.—As petals unfurl, flower coloring is generally near 46A, currant red to 46B; however, petal undersurface appears near 53C, Cardinal Red, and as flowers age, overall appearance is near 53C.

C. Petals:

(1) *Texture.*—Thick.

(2) *Appearance.*—Inside velvety and outside satiny.

(3) *Form.*—Broad fan shaped, some with notching.

(4) *Arrangement.*—Regularly arranged.

(5) *Petaloids in center.*—Few.

(6) *Persistence.*—Drop off cleanly.

(7) *Fragrance.*—Slight.

(8) *Lasting quality.*—Very long lasting quality on plant and as cut flower.

REPRODUCTIVE ORGANS

A. Stamen, filaments and anthers:

*Arrangement and color.*—Regularly arranged around styles, even length, inner ring joined at base. Color — filaments orange: anthers — yellow.

B. Pollen:

*Color.*—Yellow.

C. Styles: Medium length, even, bunched.

D. Stigmas:

*Color.*—Yellow.

E. Hips: None observed.

PLANT

A. Form: Upright, compact, bushy.

B. Growth: Very vigorous.

*Height attained.*—About 80 to 100 cm.

C. Foliage: Compound 5 leaflets (1) *Size.*—Large.

(2) *Quantity.*—Abundant.

(3) *Color.*—New foliage: Upper side — reddish purple, near 184C. Under side — reddish purple. Old foliage: Upper side — glossy green. Under side — dull green.

(4) *Shape.* —Oval, pointed.

(5) *Texture.*—Upper side is leathery, shiny, veined and under side is dull, veined and leathery.

(6) *Edge.*—Serrate.

(7) *Serration.*—Ordinary, regular.

(8) *Leaf stem.*—Color — reddish green. Under side — dull green.

(9) *Stipules.*—Medium, pointed.

(10) *Resistance to disease.*—Blackspot — very good. Mildew — excellent. Rust — very good.

D. Wood:

(1) *New wood.*—Color — reddish purple. Bark — smooth.

(2) *Old wood.*—Color — reddish green. Bark — smooth.

E. Thorns:

(1) *Thorns.*—Quantity (main stalk) — ordinary. On laterals from stalk — ordinary. Form — long, pointed. Length — medium. Color — red when young. Position — regular.

(2) *Prickles.*—Few.

F. Winter hardiness: Very winter hardy.

I claim:

1. A new and distinct variety of rose plant of the hybrid tea rose class, substantially as shown and described, characterized particularly by very well formed flowers of Currant red to Cardinal red coloring having good form and which are long lasting on the plant and as cut flowers.

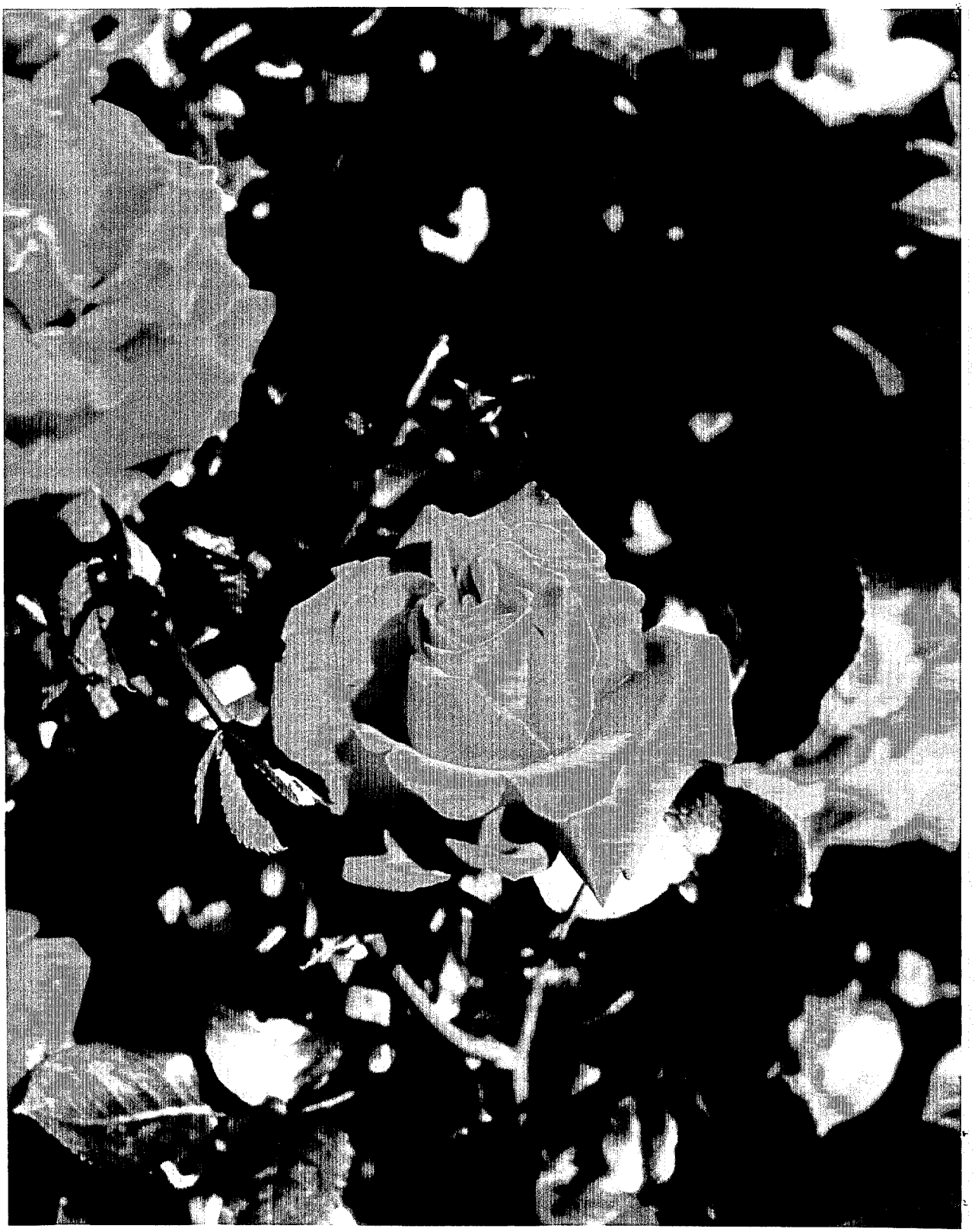

* * * * *